(12) United States Patent
Draenert

(10) Patent No.: US 6,682,566 B2
(45) Date of Patent: Jan. 27, 2004

(54) MODULAR SOCKET PROSTHESIS

(76) Inventor: Klaus Draenert, Gabriel Max Strasse 3, D-81545 Munich (DE)

( * ) Notice: Subject to any disclaimer, the term of this patent is extended or adjusted under 35 U.S.C. 154(b) by 0 days.

(21) Appl. No.: 09/919,177

(22) Filed: Jul. 30, 2001

(65) Prior Publication Data

US 2002/0049500 A1 Apr. 25, 2002

(30) Foreign Application Priority Data

Jul. 29, 2000 (DE) .......................................... 100 36 987

(51) Int. Cl.[7] .................................................. A61F 2/32
(52) U.S. Cl. .................................. 623/22.24; 623/22.21
(58) Field of Search ........................... 623/22.21, 22.24, 623/22.25, 22.28; 606/91

(56) References Cited

U.S. PATENT DOCUMENTS

| 4,172,296 A | * | 10/1979 | D'Errico | |
| 4,623,351 A | * | 11/1986 | Church | |
| 5,116,339 A | * | 5/1992 | Glock | 606/91 |
| 5,431,657 A | * | 7/1995 | Rohr | 606/91 |
| 5,507,824 A | * | 4/1996 | Lennox | |
| 5,571,201 A | * | 11/1996 | Averill et al. | |
| 5,683,399 A | * | 11/1997 | Jones | 606/91 |
| 5,879,399 A | * | 3/1999 | Church | |
| 6,132,469 A | * | 10/2000 | Schroeder | 623/22.24 |
| 6,334,875 B1 | * | 1/2002 | Keller | 623/22.28 |
| 6,352,559 B1 | * | 3/2002 | Church | 623/22.25 |

* cited by examiner

*Primary Examiner*—Ralph A. Lewis
(74) *Attorney, Agent, or Firm*—Westman, Champlin & Kelly, P.A.

(57) ABSTRACT

The present invention essentially relates to a hip joint socket system for a "press-fit" anchorage in the bony acetabulum that allows the inserts that articulate with the artificial head to be connected securely, and, using said inserts, also allows the center of the rotation of the socket to be reconstructed, the risk of luxation to be eliminated, and the plane of load application to be varied across an infinite range of positions within a defined angular range.

12 Claims, 2 Drawing Sheets

MODULAR SOCKET PROSTHESIS

BACKGROUND OF THE INVENTION

Figure 1:
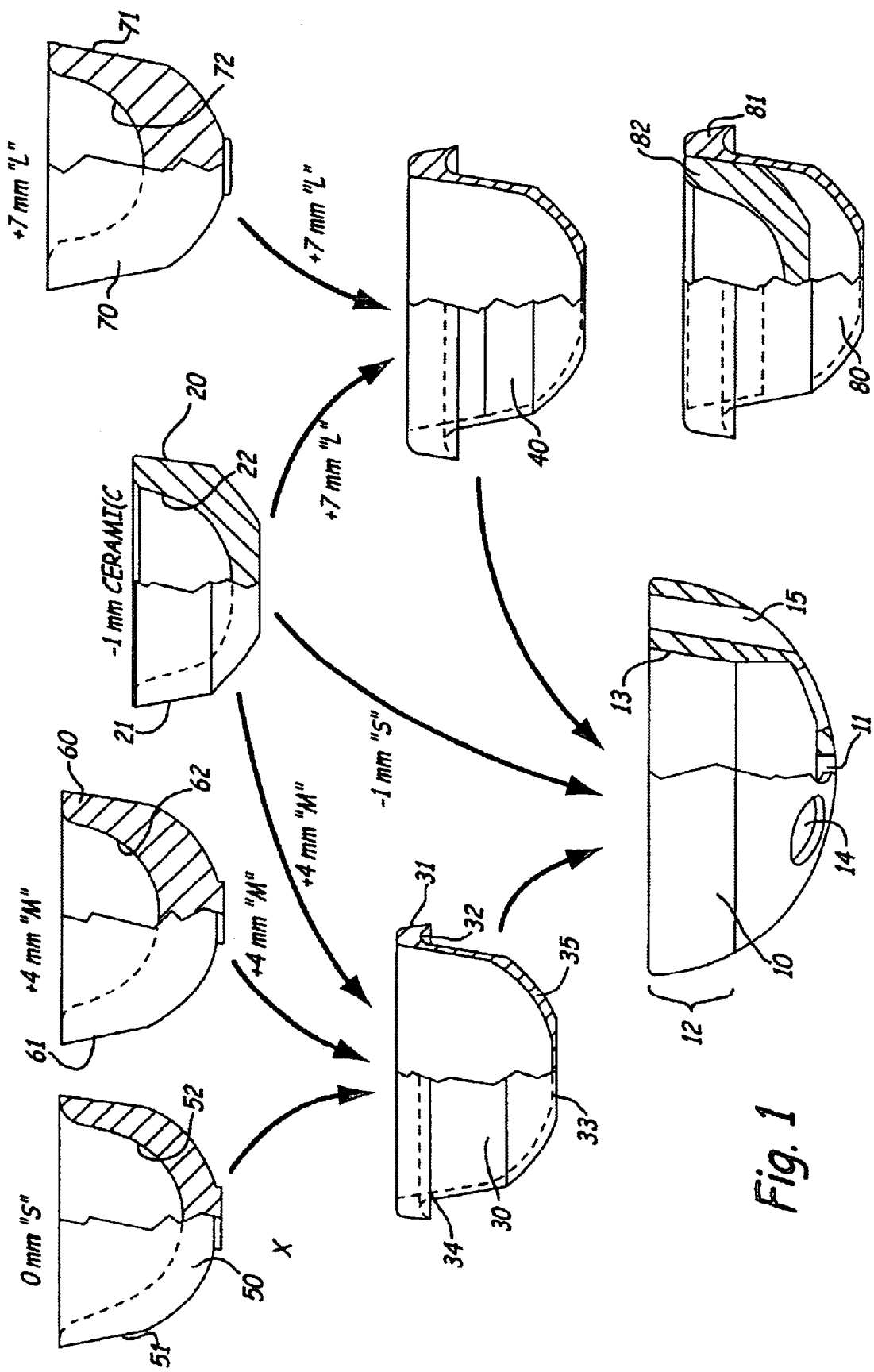

The success of the permanent anchorage of hip joint components is linked to the publications by Sir John Charnley, who cemented the components into place using bone cement, such as the publication that appeared in the *Journal of Bone and Joint Surgery*: Charnley. J., (1960), Anchorage of the Femoral Head Prosthesis to the Shaft of the Femur JBJSB 42: 28–30. The combination of the cemented plastic socket also goes back to J. Charnley (*Low Friction Arthroplasty of the Hip: Theory and Practice*, Heidelberg, N.Y., Berlin: Springer. However, combination with plastic resulted in unexpectedly high wear.

Therefore, researchers attempted to find combinations for the articulation that could be expected to have low wear. Industrial experience told them that the smoothest surfaces could be achieved with ceramics. The articulation of ceramic against ceramic currently allows one to expect wear that will be 200 times less than that with a polyethylene-metal head. However, such an articulation has a problem: Ceramic cannot be subjected to flexural or shear loads.

The combination of ceramic and ceramic led to the development of metal implants that protected the ceramic from flexural and shear loads and that could be anchored by press-fitting them into bones. This surface press-fit, which can also be ground with diamond-faced tools (PA D 199 60 707.9) does lower the center of rotation (CR) of the socket into the lower area of the acetabulum, and this leads to a medialization of the leg—a displacement inwards. In order to prevent this, researchers have been trying the reconstruct the CR. This was successful in the present invention.

Prior Art

There are various ways to anchor the socket. One of the most commonly used is to cement in an UHMWPE (Ultra-High-Molecular-Weight PolyEthylene) socket with bone cement, as described above. It was assumed that cementing the socket would be governed by the same laws and therefore have the same success as cementing the femur component. This was not the case. The socket is cemented under very different conditions. The plastic socket is cemented onto a relatively dense bone, which means that the bone cement cannot penetrate at all into the bone if no anchorage holes have been made. Such anchorage holes, however, represent hourglass connections that do not provide sufficient anchorage since the spongiosa structure in the acetabulum initially has a closely spaced honeycomb, which becomes more widely spaced as one moves in the proximal direction toward the spinal column/pelvis connection. Filling occurs "against" the morphological structure, and as a result both the rigidification of the bone structure as well as the anchorage—the so-called interlocking—is inadequate.

Successful attempts have been made to grind open the dense top of the socket without destroying the stability of the lightweight design (sandwich construction). However, a diamond instrument must be used for this purpose, and the bone cement must be drawn in. Since this technology has only become available recently (DPA 199 60 707.9), and since one also has to deal with the wear problem encountered in plastic sockets, researchers have recently been trying to test other potential anchorage systems.

One of the most commonly used of these systems is the so-called screw principle, in which the artificial socket is cut directly into the bone without an attachment means and is screwed down. However, the screw threads result in bone necrosis and pelvis fractures.

Attempts were also made to enlarge the anchoring surface in the bone and to allow the bone to grow in (porous ingrowth principle), but here too the loosening rate was high, and the implant became encapsulated in the interconnective tissue. Combining this approach with a threaded connection also failed to solve the problem.

Researchers first had to study the morphology and the function of the lunate fascia—the crescent-moon-shaped articular surface of the socket. This led to a physiological anchorage principle: the principle of providing pretension in the bone. This was not new, but it was easy to implement in the case of the socket since the deformation of the joint surface is nearly concentric.

It was therefore possible to press-fit a nearly spherical component in the acetabulum, the name used for the socket when it is located in the pelvis. The details of such a socket are described in DPA 100 03 543.4.

The surface press-fit necessitates that the socket be blocked over a large area behind the equator of a virtual socket ball; when this is done, the center of rotation is always moved downward into the socket. This was not given due attention, but it can also be an advantage for the bony anchorage, since the lever arms for a tipping movement are shorter—in other words, the so-called socket offset is shorter. But in any event it means that the leg as a whole is medialized further, which can result in pelvitrochanterian insufficiency. This means that the muscles become relatively long and have an unfavorable lever arm. For this reason, attempts were made to find solutions that combine fixed seating with a reconstruction of the position of the center of rotation. EP 0 694 294 B1 describes an insert which, upon first examination, appears to be able to accomplish this goal, but in fact it cannot. The object of that invention is to loosen the joint socket from the exterior surface cone, where a margin is used as an opposing bearing, which allows the outward bracing. An insert of this type cannot be used for the invention described below since abutment on the perimeter of the shell prevents a press-fit seat. However, the following invention was able to solve this problem simply and elegantly.

DESCRIPTION OF THE INVENTION

The invention comprises a modular implant that has an outer shell as shown in FIG. 01/10. This outer shell is flattened at the topdome (FIG. 01/11), and has a spherical band that is the anchoring zone (FIG. 01/12). The inside contour corresponds to a precise cone having a defined angle (FIG. 01/13). The surface of the titanium socket that is represented in this example has a roughness of 80–100 microns (FIG. 02/16), and the surface of the cone has a defined undulation for holding the ceramic (FIG. 01/20) or the insert module (FIG. 01/30) and (FIG. 01/40).

The shell (FIG. 01/10), which in this case is made of titanium, has perforations in its topdome to reduce the mass and to increase the overall elasticity of the design (FIG. 01/14). The holes in the wall of the titanium implant (FIG. 01/15) have cushioning properties relative to the bone, as can be shown by finite element calculations.

The module, which can be inserted in the titanium shell (FIG. 01/10) and which is made of the same material (FIG. 01/30), has an annular support (FIG. 01/31) that is designed in such a way (FIG. 01/32) that a concentration of stress does not occur at the point where the spherical shell is attached. The base (FIG. 01/33) of the module is open; the cone (FIG.

01/34) has a surface that is specifically undulated to hold the ceramic insert and is undercut (FIG. 01/35), to achieve subsidence, a term that refers to the self-setting ability of the implant. In order to achieve long-term stability, the module and the articulating insert can be rigidly connected to each other (FIG. 01/80).

The module (FIG. 01/30) thereby experiences a relative change in the offset of 0 mm relative to the pure ceramic insert (FIG. 01/20) of −1 mm; and the module (FIG. 01/60) may have an offset of +4 mm. The offset in a socket refers to the distance from the median plane to the center of rotation, and it is inherent in this definition that the topography of the physiological center rotation is defined as a 0 mm. A module having an offset of 7 mm has also been designed, as shown in FIG. 01/40. The module may be constructed of a single piece and it may be rigidly attached with components made of ceramic, HDPE, metal, or some other abrasion-resistant material, which would be advantageous.

In the case of the titanium/HDPE versions, this change in the offset is easier to incorporate in the design of the HDPE insert, as is shown in FIGS. 01/50, 01/60, and 01/70. The conical exterior of the insert (FIG. 01/61) has a specific undulation for the mounting area in the titanium insert. This undulation holds the plastic insert in an interlocking manner, FIG. 01/30 and FIG. 01/40. The interior surfaces of the plastic insert have a specific smoothness; in the case of the one-part design, they are rigidly connected to the metal.

Figure 4:
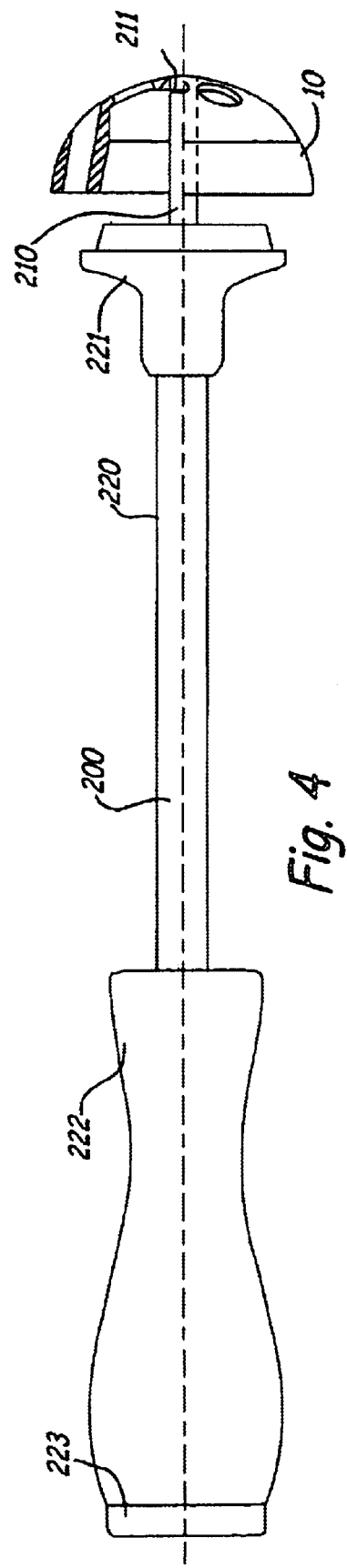

FIG. 4 illustrates a setting instrument for the atraumatic-press fit anchoring of the socket in the patient's pelvis. The instrument 200 includes a handle assembly 220 having a handle 222 at one end provided with a mallet impact element 223 and an end piece 221 at its opposite end. The end piece 221 has a conical end that can fit in the conical entry of the outer shell 10. A central rod 210 projects from the handle assembly 220 beyond the end piece 221 and is provided at its free end 211 with means for attaching the shell 10 to the setting instrument. The central rod 210 is moveable in the impact direction relative to the handle assembly with a spring like action. The central rod to project beyond the end piece 221.

EXAMPLE

A patient having advanced coxarthrosis is positioned on the operating table in the usual manner and, after the surgical area has been covered and prepared using sterile techniques, the hip joint is exposed, for example by means of a lateral access, the capsule is opened, the femur is dislocated, and the head of the femur is removed and lifted away. Following this, the hip socket is adjusted and the cartilage is removed using a sharp ruffle fluted cutter.

Figure 3:
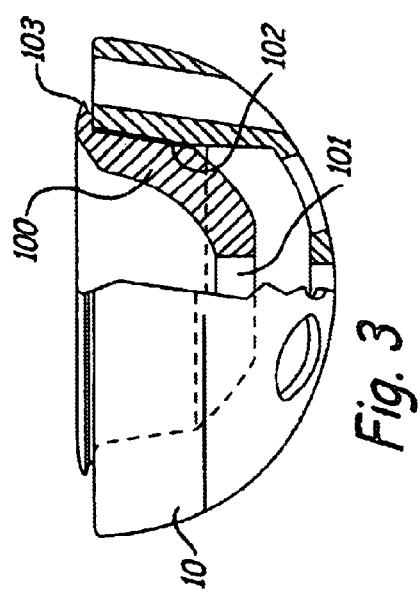

As soon as the bone has been exposed, the fluted cutter is replaced with a diamond cutter and, using the same size as the head, the bed is ground open spherically. The next larger size diamond grinder is used to cut down to the bottom of the socket until the edge of the spherical hollow grinding tool disappears into the socket. A titanium shell is now screwed on to the setting instrument (FIG. 04), and the setting instrument is positioned in the ground-out bed of the socket and is hammered into place in the bone bed in a position having an anteversion of 8° and an entry plane angle of inclination of 38°. The press-fit seat of the socket shell is absolutely secure in all cases. The setting instrument is unscrewed, and a trial insert is installed (FIG. 03/100). The plastic trial insert is available in all versions of the module, and is clearly identified, for example, by various colors.

The base of the trial insert has an opening (FIG. 03/101). The support surface (FIG. 03/102) has a conical shape that corresponds to the socket shell, and the support around the circumference of the shell is in the form of a large lip (FIG. 03/103). The trial insert can be easily removed.

The femur is then prepared and a component is inserted. Then a trial head is placed on it and repositioned. The luxation tendency and the positioning of the centers of rotation for the socket and the femur are checked carefully, if need be using an imaging device. After checking is finished, the trial insert is replaced with a titanium/ceramic module. This module can be of a two-part design or, preferably, a one-part design. Then the final ceramic head is installed.

The operation is then completed by inserting drainages, suturing up muscles and fasciae, and closing up the wound.

MODULAR SOCKET REPLACEMENT

FIG. 01

FIG. 01/10 Metal shell (titanium) for anchoring in the pelvis, with a flattened area in portions FIG. 01/11 Holes in the bottom of the socket and a FIG. 01/12 band-shaped, spherical surface-press-fit anchoring zone having a FIG. 01/13 precise conical mounting surface for the insert and FIG. 01/14 one or more holes in the bottom of the socket, FIG. 01/15 and holes through the outer wall arranged in a circle around the equator FIG. 01/20 Ceramic insert with press fit in (FIG. 01/13) achieved by the FIG. 01/21 precision-ground cone and the FIG. 01/22 precision-ground, spherical articulation having the greatest possible surface smoothness FIG. 01/30 Metal module (titanium) for the shell (FIG. 01/10) having FIG. 01/31 a support on the shell entry, and FIG. 01/32 a structure for avoiding a specified fracture point and FIG. 01/33 an opening in the base, and FIG. 01/34 a precision conical mounting surface for the insert (FIG. 01/20) or other having an offset of up to 4 mm, and a FIG. 01/35 rounded socket bottom FIG. 01/40 Metal module for HDPE and ceramic inserts having an offset of up to 7 mm FIG. 01/50 HDPE insert in the module (FIG. 01/30) having a FIG. 01/51 precision cone and a FIG. 01/52 precision articular surface of the greatest possible smoothness for accepting a ball having a 0 mm insert offset FIG. 01/60 HDPE insert for the module (FIG. 01/30) having analogous features at (FIG. 01/51) and (FIG. 01/52) analogous to (FIG. 01/61 and FIG. 01/62) and having an offset of 4 mm FIG. 01/70 HDPE insert for the module (FIG. 01/40) having analogous features at (FIG. 01/71) and (FIG. 01/72) analogous to (FIG. 01/51 and FIG. 01/52) and having an offset of 7 mm FIG. 01/80 Single-piece module comprising a ceramic inlet rigidly press-fit (FIG. 01/81) in position and a metal back (FIG. 01/82).

Figure 2:
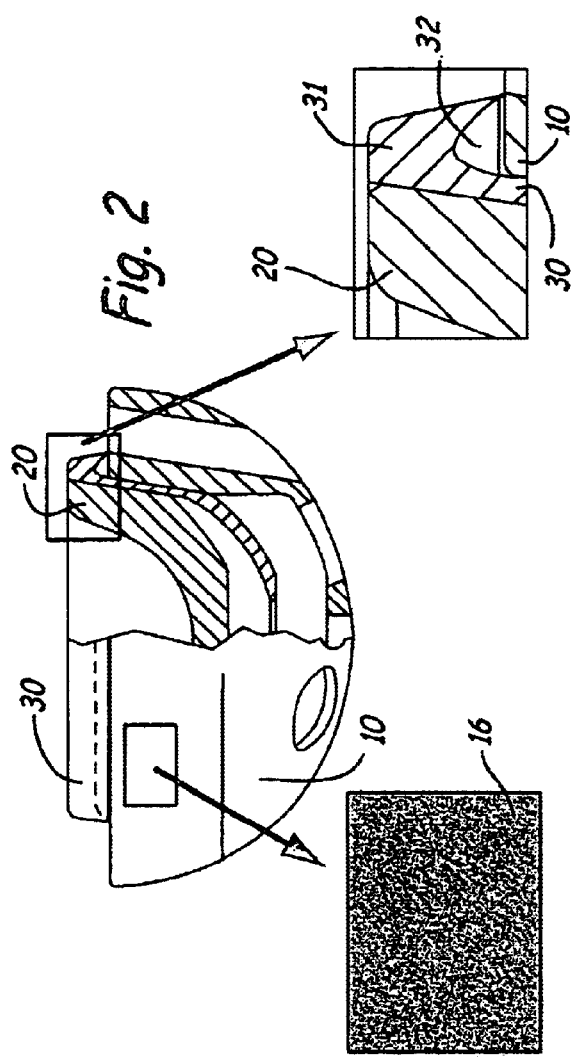

FIG. 02 Metal shell (FIG. 2/10) having an isogenic module (FIG. 02/30) for accepting a ceramic insert (FIG. 02/20), for example, having a FIG. 02/16 surface roughness of 50 to 140 μm, preferably 80 to 100 μm FIG. 03 Metal shell (FIG. 03/10) having a trial insert (FIG. 03/100) having a FIG. 03/101 perforated base and FIG. 03/102 precision cone for accepting a shell, and FIG. 03/103 Collar support providing modest undercut for removal purposes FIG. 04 Setting instrument (FIG. 04/200), having a FIG. 04/210 central rod, having a FIG. 04/211 support for the socket shell, and FIG. 04/220 handle assembly, having a FIG. 04/221 shell end piece, and FIG. 04/222 handle, FIG. 04/223 mallet impact point

What is claimed is:

1. An artificial hip socket comprising:
   an outer shell adapted to be fitted in a patient's pelvis, the outer shell having a conical interior surface defining an interior cavity, and a rim that surrounds the interior cavity;
   an insert module that can be fitted in the outer shell, the insert module having a conical exterior surface that matches the conical interior surface of the outer shell, the insert module having a collar that extends over the rim of the outer shell when the insert module is fitted in the outer shell; and
   an articulating insert that is separate from the insert module and can be fitted in the insert module, the articulating insert having an interior cavity for receiving a femur head.

2. An artificial hip socket according to claim 1, wherein the outer shell defines an interior cavity that is bounded by said conical interior surface and by a flattened dome.

3. An artificial hip socket according to claim 1, wherein the cone angle of said conical interior surface is between 3° and 15°.

4. An artificial hip socket according to claim 1, wherein the outer shell is made of titanium, a titanium alloy, tantalum, a tantalum alloy, a CoCrMo alloy, or stainless steel, the insert module is made of the same material as the outer shell and the articulating insert is made of ceramic or plastic.

5. An artificial hip socket according to claim 1, further comprising a trial insert that can be fitted into and removed from the outer shell.

6. An artificial hip socket according to claim 1, wherein the outer shell includes a formation for attaching the outer shell to a setting instrument for anchoring the shell in a patient's pelvis.

7. An artificial hip socket according to claim 1, wherein the outer shell has a peripheral wall formed with passages that permit elastic deformation of the outer shell.

8. An artificial hip socket comprising:
   an outer shell adapted to be fitted in a patient's pelvis, the outer shell having a conical interior surface;
   an insert module that can be fitted in the outer shell, the insert module having a conical exterior surface that matches the conical interior surface of the outer shell, the insert module having a conical interior surface, and
   an articulating insert that is separate from the insert module and can be fitted in the insert module, the articulating insert having a conical exterior surface that matches the conical interior surface of the insert module, and the articulating insert having an interior cavity for receiving a femur head.

9. An artificial hip socket comprising:
   an outer shell adapted to be fitted in a patient's pelvis, the outer shell having a conical interior surface,
   an insert module that can be fitted in the outer shell, the insert module having a conical exterior surface that matches the conical interior surface of the outer shell, and
   an articulating insert fitted in the insert module, the articulating insert having an interior cavity for receiving a femur head and being made of a different material from the insert module, wherein the insert module has a conical interior surface and the articulating insert has a conical exterior surface that matches the conical interior surface of the insert module.

10. An artificial hip socket according to claim 9, wherein the outer shell is made of titanium, a titanium alloy, tantalum, a tantalum alloy, a CoCrMo alloy, or stainless steel, the insert module is made of the same material as the outer shell and the articulating insert is made of ceramic or plastic.

11. An artificial hip socket according to claim 9, wherein the outer shell has a peripheral wall formed with passages that permit elastic deformation of the outer shell.

12. A method of assembling an artificial hip socket, comprising:
   a) providing an outer shell adapted to be fitted in the patient's pelvis, the outer shell having a conical interior surface,
   b) fitting a trial insert in the outer shell and subsequently removing the trial insert,
   c) fitting an insert module in the outer shell, the insert module having a conical exterior surface that matches the conical interior surface of the outer shell, and
   d) fitting an articulating insert in the insert module, the articulating insert having an interior cavity for receiving a femur head.

* * * * *